(12) United States Patent
Zhong et al.

(10) Patent No.: US 10,684,340 B1
(45) Date of Patent: Jun. 16, 2020

(54) SYSTEMS AND METHODS FOR PREDICTING ERRORS AND OPTIMIZING PROTOCOLS IN QUANTITATIVE MAGNETIC RESONANCE IMAGING

(71) Applicants: Siemens Healthcare GmbH, Erlangen (DE); Duke University, Durham, NC (US)

(72) Inventors: Xiaodong Zhong, Lilburn, GA (US); Marcel Dominik Nickel, Herzogenaurach (DE); Stephan Kannengiesser, Wuppertal (DE); Brian Dale, Morrisville, NC (US); Berthold Kiefer, Erlangen (DE); Mustafa R. Bashir, Cary, NC (US)

(73) Assignees: Siemens Healthcare GmbH, Erlangen (DE); Duke University, Durham, NC (US)

( * ) Notice: Subject to any disclaimer, the term of this patent is extended or adjusted under 35 U.S.C. 154(b) by 0 days.

(21) Appl. No.: 16/242,353

(22) Filed: Jan. 8, 2019

(51) Int. Cl.
| | | |
|---|---|---|
| *G01R 33/56* | (2006.01) | |
| *G01R 33/563* | (2006.01) | |
| *A61B 5/00* | (2006.01) | |
| *A61B 5/055* | (2006.01) | |
| *G01R 33/565* | (2006.01) | |

(52) U.S. Cl.
CPC .......... *G01R 33/5608* (2013.01); *A61B 5/055* (2013.01); *A61B 5/7203* (2013.01); *G01R 33/565* (2013.01); *G01R 33/56341* (2013.01)

(58) Field of Classification Search
CPC .......... G01R 33/5608; G01R 33/56341; G01R 33/565; A61B 5/7203; A61B 5/055
See application file for complete search history.

(56) References Cited

U.S. PATENT DOCUMENTS

| | | | | |
|---|---|---|---|---|
| 2015/0168527 A1* | 6/2015 | Topgaard | ......... | G01R 33/56341 600/419 |
| 2016/0084929 A1* | 3/2016 | Dale | .................. | G01R 33/5608 324/309 |

OTHER PUBLICATIONS

D. Lebihan et al., "Separation of diffusion and perfusion in intravoxel incoherent motion MR imaging," Radiology 1988;168;497-505.

\* cited by examiner

*Primary Examiner* — G. M. A Hyder (57) ABSTRACT

A magnetic resonance imaging system and method are provided for improved determination of noise bias effects in calculating fitted parameters for quantitative MRI procedures. The system and method includes selecting a range for the SNR and fitted parameter values, and for each of a plurality of base pairs of these values and for a plurality of b values, adding a random noise term to the real and imaginary components of a plurality of corresponding signal terms, fitting magnitudes of the resulting "noisy" signals to determine a "noisy" fitted parameter value, and compare the "noisy" and base fitted parameter values to determine a noise-based error for each pair of base values. The noise-based errors can be used to generate an error map, modify imaging parameters to reduce such errors, or correct fitted parameters directly.

18 Claims, 6 Drawing Sheets

SYSTEMS AND METHODS FOR PREDICTING ERRORS AND OPTIMIZING PROTOCOLS IN QUANTITATIVE MAGNETIC RESONANCE IMAGING

FIELD OF THE DISCLOSURE

The present disclosure relates to a method and a system for predicting errors and reducing and/or correcting such errors in quantitative magnetic resonance imaging including, more specifically, improved diffusion imaging of tissue affected by noise bias.

BACKGROUND INFORMATION

Magnetic resonance (MR) imaging is a known technology that can produce images of the inside of an examination subject without radiation exposure. In a typical MR imaging procedure, the subject is positioned in a strong, static, homogeneous base magnetic field BO (having a field strength that is typically between about 0.5 Tesla and 3 Tesla) in an MR apparatus, so that the subject's nuclear spins become oriented along the base magnetic field.

Radio-frequency (RF) excitation pulses are directed into the examination subject to excite nuclear magnetic resonances, and subsequent relaxation of the excited nuclear magnetic resonances can generate RF signals. Rapidly switched magnetic gradient fields can be superimposed on the base magnetic field, in various orientations, to provide spatial coding of the RF signal data (also referred to as image data). The RF signal data can be detected during a 'readout' phase, and mathematically processed to reconstruct images of the examination subject. For example, the acquired RF signal data are typically digitized and stored as complex numerical values in a k-space matrix. An associated MR image can be reconstructed from the k-space matrix populated with such values using a multi-dimensional Fourier transformation.

Figure 1:
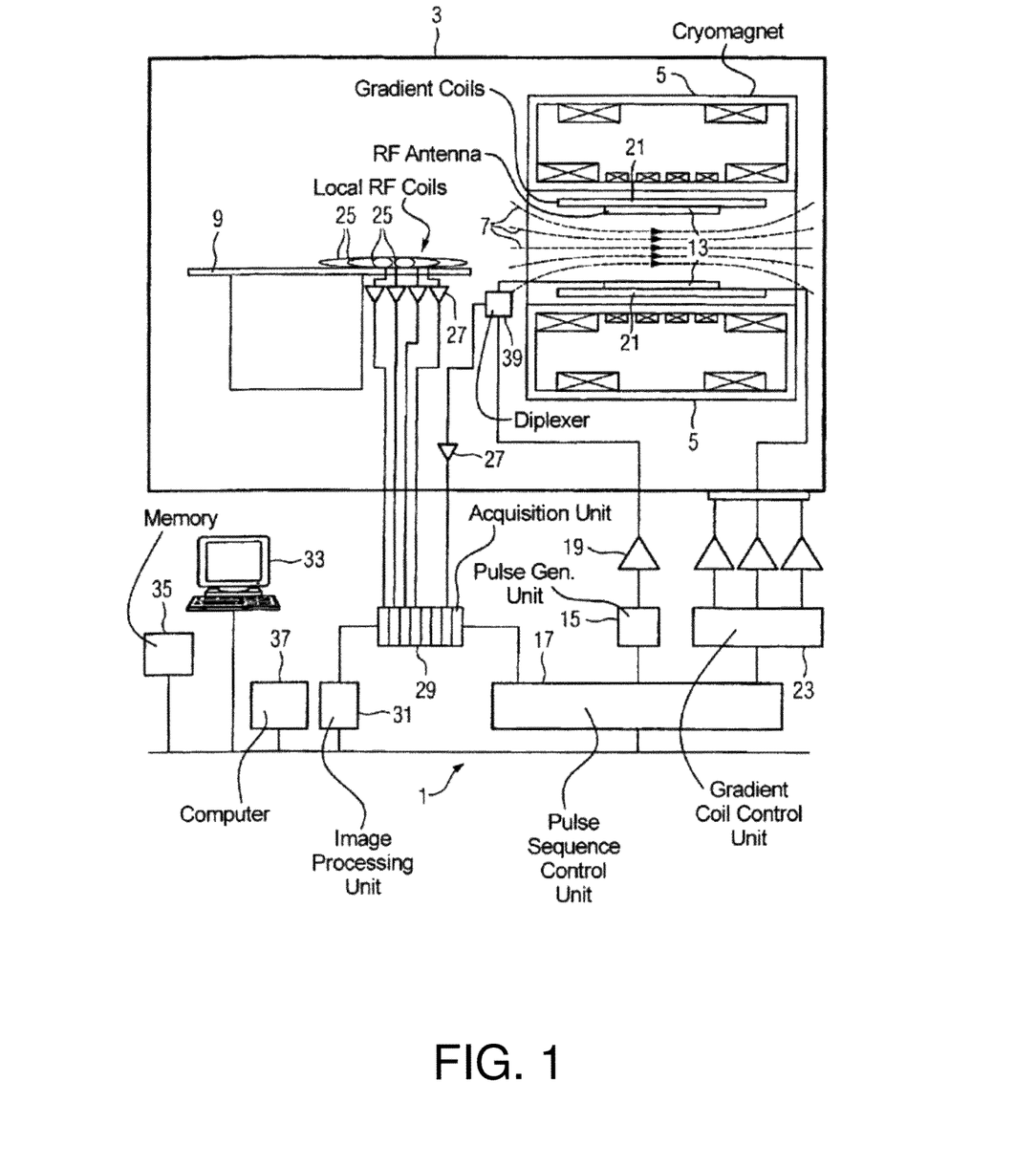
FIG. 1 schematically illustrates the basic components of a magnetic resonance imaging system constructed and operating in accordance with embodiments of the present disclosure.

FIG. 1 schematically shows the design of a magnetic resonance system 1 with certain components in accordance with embodiments of the present disclosure. The MR system 1 is configured, inter alia, to provide various magnetic fields tuned to one another as precisely as possible in terms of their temporal and spatial characteristics to facilitate examination of portions of a subject's body using magnetic resonance imaging techniques.

A strong magnet 5 (typically a cryomagnet) having a tunnel-shaped opening is provided in a radio-frequency (RF) shielded measurement chamber 3 to generate a static, strong base (or polarizing) magnetic field 7. The strength of the base magnetic field 7 is typically between 0.5 Tesla and 3 Tesla, although lower or higher field strengths can be provided in certain embodiments. A body or a body part to be examined (not shown) can be positioned within the substantially homogeneous region of the base magnetic field 7, e.g., provided on a patient bed 9.

Excitation of nuclear spins of certain atoms within the body can be provided via magnetic RF excitation pulses that are radiated using an RF antenna 13, such as a body coil. Other configurations of RF coils or antennas can also be provided in further embodiments, and such configurations may be adapted for particular portions of the subject anatomy to be imaged. The RF excitation pulses are generated by a pulse generation unit 15 that is controlled by a pulse sequence control unit 17. After an amplification by a radio-frequency amplifier 19, the RF pulses are relayed to the RF antenna 13. The exemplary RF system shown in FIG. 1 is a schematic illustration, and particular configurations of the various components may vary from that illustrated in exemplary embodiments of the disclosure. For example, the MR system 1 can include a plurality of pulse generation units 15, a plurality of RF amplifiers 19, and/or a plurality of RF antennas 13 that may have different configurations depending on the body parts being imaged.

The magnetic resonance system 1 further includes gradient coils 21 that can provide directionally and temporally varied magnetic gradient fields for selective excitation and spatial encoding of the RF signals that are emitted and/or received by the RF antenna(s) 13. The gradient coils 21 are typically oriented along the three primary axes (x- y- and z-directions), although other or additional orientations may be used in certain embodiments. Pulsed current supplied to the gradient coils 21 can be controlled by a gradient coil control unit 23 that, like the pulse generation unit 15, is connected with the pulse sequence control unit 27. By controlling the pulsed current supplied to the gradient coils 21, transient gradient magnetic fields in the x-, y-, and z-directions can be superimposed on the static base magnetic field BO. This makes it possible to set and vary, for example, the directions and magnitudes of a slice gradient magnetic field Gs, a phase encode gradient magnetic field Ge, and a read (frequency encode) gradient magnetic field Gr, which can be synchronized with emission and detection of RF pulses. Such interactions between RF pulses and transient magnetic fields can provide spatially selective excitation and spatial encoding of RF signals.

RF signals emitted by the excited nuclear spins can be detected by the RF antenna 13 and/or by local coils 25, amplified by associated radio-frequency preamplifiers 27, and processed further and digitized by an acquisition unit 29. In certain embodiments where a coil 13 (such as, for example, a body coil) can be operated both in transmission mode and in acquisition mode (e.g, it can be used to both emit RF excitation pulses and receive RF signals emitted by nuclear spins), the correct relaying of RF energy is regulated by an upstream transmission-reception diplexer 39.

An image processing unit 31 can generate one or more images based on the RF signals that represent image data. Such images can be presented to a user via an operator console 33 and/or be stored in a memory unit 35. A processor arrangement 37 can be provided in communication with the memory unit 35, and configured to execute computer-executable instructions stored in the memory unit 35 to control various individual system components. For example, the processor arrangement 37 can be configured by programmed instructions to control components such as, e.g., the gradient coil control unit 23, the pulse generation unit 15, and/or the pulse sequence control unit 27 to generate particular sequences of RF pulses and magnetic field variations, process and/or manipulate image data, etc., according to exemplary embodiments of the disclosure described herein.

Magnetic resonance imaging is a versatile modality which allows not only qualitative organ or tissue anatomical evaluation but also quantitative assessment of tissue characteristics. For example, diffusion MRI, which includes diffusion-weighted imaging (DWI) and diffusion tensor imaging (DTI), is a quantitative imaging technique that can provide certain quantitative information on specific features of imaged tissues.

Diffusion MRI is generally based on the Brownian motion of water molecules. It can provide certain contrasts and characterizations among tissues at a cellular level in vivo and non-invasively. Because the diffusion rate of water molecules in different tissues correlates with their physiological state, and may be altered in diseased tissues, DWI has a very important role in clinical applications. For example, an early and widely-used application of DWI is to diagnose acute ischemic stroke in the brain.

In diffusion-weighted (DW) images, the intensity of each pixel reflects an estimate of the water diffusion rate at that pixel, and also the tissue structure in which the water molecules diffuse. This pixel intensity is attenuated according to the diffusion weighting (b-value) and direction of the diffusion gradients. The DW image intensity can be described by the Intra Voxel Incoherent Motion (IVIM) model, where both the pure molecular-based diffusion process and the perfusion-based diffusion process related with the incoherent microcirculation contribute to the signal attenuation, where this signal attenuation has been observed to exhibit an approximately exponential decay. The IVIM model is described, e.g., in LeBihan D, Breton E, Lallemand D, Aubin M L, Vignaud J, Laval-Jeantet M., "Separation of diffusion and perfusion in intravoxel incoherent motion MR imaging," *Radiology* 1988; 168:497-505.

In practice, if two or more DW images with different b-values are acquired, a so-called apparent diffusion coefficient (ADC) map can be calculated as a single "effective" coefficient to simplify the characterization of different mechanisms in the diffusion process. The ADC corresponds to the exponential coefficient in the signal model describing signal loss with increasing b value. Unlike individual DW images, the ADC map is insensitive to the influence of T1 and T2/T2* effects and provides voxel-by-voxel ADC values as a property of the tissue; thus the ADC is regarded as a quantitative measure of the diffusion behavior in tissue. Further, ADC maps can be averaged from three orthogonal orientations to yield an overall $ADC_{trace}$ map, which further removes diffusion orientation dependence.

The signal-to-noise ratio (SNR) tends to be relatively low in DW images as compared to other image contrasts, in large part because of T2/T2* effects and the diffusion weighting. This low SNR poses a challenge for ADC quantification, as the SNR of high b-value DW images may be close to or below the noise floor. In practice, high b-values often have to be used, and low SNR cannot be avoided. In addition, some organs such as the liver typically have a lower SNR in high b-value DW images than other anatomic regions. The noise in the high b-value images, if not accounted for, can lead to significant errors in the resultant ADC map.

Several factors can affect the SNR during acquisition of MR image data, many of which can be controlled or selected by an operator. These factors include image resolution (e.g., slice thickness, size of the image matrix, and field of view), scan parameters (such as TR, TE, and flip angle), magnetic field strength, and coil selection/geometry.

For example, it is generally observed that the SNR in MR imaging will increase with decreasing resolution of the image data. Larger SNR values can lead to more accurate calculation of ADC values and other quantitative MR imaging parameters. However, the decreased image resolution is generally undesirable. For example, decreased image resolution (which corresponds to larger pixels or voxels) may fail to sufficiently distinguish tissue features and variations in the imaged region. Further, because parameters such as the ADC typically are dependent in part on tissue type, low-resolution/high-SNR image data can fail to properly measure localized values of such parameters, e.g., averaging different values of the ADC from different tissues present in a single pixel/voxel. This undesirable spatial averaging can inhibit or prevent obtaining an accurate ADC map having sufficient spatial resolution. Thus, there is an inherent trade-off between decreasing the spatial resolution of the DW image data to increase the SNR, and decreasing the localization and accurate spatial variations of the parameters to be determined (such as the ADC), thereby resulting in less-accurate parameter maps.

Similarly, other quantitative techniques in MRI are also influenced by the noise effects. Such quantitative property maps include, but are not limited to, calculated T2, R2, T2* or R2* maps using spin echo (SE), turbo/fast spin echo (TSE/FSE) or gradient echo (GRE) MRI, respectively, calculated T1 maps using SE, TSE/FSE or Turbo FLASH MRI, and calculated proton density fat fraction (PDFF) and proton density water fraction (PDWF) maps using GRE MRI. Although the present disclosure primarily focuses on calculations and results relating to ADC measurement and values, the same approach and methods can be used for other quantitative MRI procedures such as those mentioned above.

Background Theory

To provide a more complete basis for understanding the inventive systems and methods described herein, an overview of the basic equations of the signal model for calculating ADC values using quantitative MRI will now be summarized. First, for the MR image data acquisitions used to calculate an ADC map, all imaging parameters except the b-values, e.g. TR and TE, are kept essentially constant so that common factors such as T1 and T2/T2* effects can be ignored in the signal model. For the n acquisitions with varying b-values, the general equations of the acquired MR signal are given by $$S_1 = S_0 e^{-b_1 \cdot ADC}$$

$$\ldots,$$

$$S_n = S_0 e^{-b_n \cdot ADC} \quad [1]$$

where $S_0$ represents a voxel intensity without diffusion weighting, e.g., with b=0. The set of equalities in Equation [1] has two unknown variables, $S_0$ and ADC, and these values can be determined using at least two DW MR image acquisitions obtained with different b-values.

Various techniques for fitting MR diffusion data to obtain an ADC map have been described in the literature and used in practice. The most widely accepted method is the log-linear (LL) fitting method. By taking the log of both sides of Eq. [1], and defining $y_i$ as $$y_i = \log(S_i), \quad [2]$$

Eq. [1] can be written in the form $$y_1 = \log(S_0) - ADC \cdot b_1$$

$$\ldots$$

$$y_n = \log(S_0) - ADC \cdot b_n \quad [3]$$

If we further define:

$$x_i = b_i, \quad [4]$$

$$\bar{y} = \frac{\sum_{i=1}^{n} y_i}{n}, \quad [5]$$

and $$\bar{x} = \frac{\sum_{i=1}^{n} x_i}{n},\quad [6]$$

then the ADC can be calculated as $$ADC = \frac{n\bar{x}\bar{y} - \sum_{i=1}^{n} x_i y_i}{\sum_{i=1}^{n} x_i^2 - n\bar{x}^2}.\quad [7]$$

Another common approach for solving for the unknown variables in non-linear equations is the least-squares (LS) non-linear fitting method. The least-squares non-linear fitting method can be summarized as a solution that minimizes the sum of the squares of the errors (E) for the fitted data points. For example, the LS method can be used to determine the two unknown variables in Equation [1], $S_0$ and ADC, by minimizing E, where E is defined as $$E = \sum_{i=1}^{n} |S_i - F_i|^2,\quad [8]$$

and where $F_i$ is defined as $$F_i = m_0(b_i),\quad [9]$$

with $$m_0(b_i) = S_0 e^{-b_i \cdot ADC}.\quad [10]$$

With sets of diffusion image data obtained using at least two different b-values, there are various least squares non-linear techniques known in the art (and in the general field of nonlinear mathematics) that can be used to determine values of $S_0$ and ADC that minimize E in Equation [8]. For example, the Levenberg-Marquardt algorithm, also known as the damped least-squares method, can be used. Other conventional least-squares solution techniques may also be used to solve Equation [8].

Signal intensities in an MR image are often corrupted by noise. In MRI image data, which is naturally complex data, the noise distribution has generally been observed to be well-represented by a symmetrical Gaussian or normal distribution. However, in DWI procedures, only the magnitude of the signal data is typically used in ADC calculations, e.g., the $S_i$ values represent only the magnitude without the phase. This conversion from complex data to magnitude values causes the noise distribution for the magnitude data to be changed to an asymmetric Rician distribution, or more generally, non-central chi-squared distribution for multi-channel coils. As a result, signal intensities at low SNR can exhibit a systematic bias related to the noise, the magnitude of which appears as a value ($m_{bias}$) that is higher than the noise-free true value of the magnitude ($m_0$). If this effect is not properly accounted for, the fitted estimates of the ADC will tend to be biased when the SNR of the obtained image data is low.

U.S. Patent Publication No. 2016/0084929 of Dale et al. describes a technique to correct such noise effects for signal magnitude data that includes three different noise-biased data models ($m_{MP}$, $m_{MD}$ and $m_{EX}$) and two different approaches for processing the noise-biased data (referred to therein as the Forward Approach and the Backward Approach). In the present disclosure, $m_{MP}$ and the Backward Approach are used, in addition to the log-linear and least-squares fitting techniques described herein above, to further illustrate examples of the methods described herein.

In practice, multiple DW image datasets corresponding to a high b-value can be obtained and averaged. Such averaging can increase the effective SNR (e.g., by averaging out some of the noise effects) such that the averaged high b-value DW image data can have sufficient SNR to perform fitting methods such as LL and LS more accurately. However, this averaging approach suffers from a bias in the resultant ADC value, because the source data of the high b-value DW images are contaminated by noise having a non-zero expectation value. Thus, the averaged images (typically averaged using the magnitude images of all the repetitions obtained for a particular b-value) still exhibit systematic errors in the image intensity.

Accordingly, it would be desirable to have a method for improved quantitative MRI in which the effects of inherent signal noise on measured parameters for a particular fitting scheme can be better predicted. Such information can be used, e.g., to facilitate acquisition of improved parameter maps by selection of optimal imaging parameters and/or to generate improved parameter maps directly by applying such predicted noise effects to the fitted/calculated parameter values.

SUMMARY OF EXEMPLARY EMBODIMENTS

Exemplary embodiments of the present disclosure can provide a system method for estimating errors in fitted parameters for quantitative MRI procedures, obtaining improved parameter maps using quantitative MR imaging, for optimizing imaging protocols, and for providing error correction factors to yield more accurate fitted values of quantitative MRI parameters. Embodiments of the disclosure provide a method for predicting and estimating errors resulting from noise effects in the image data with low SNR that arise from any known or conventional fitting/calculation procedure to calculate the quantitative mapped parameters.

In exemplary embodiments of the present disclosure, a method is provided for calculating errors in fitted MRI parameters based on simulation of noise effects in the data. Such method can include the following steps:
 a) Selecting at least 2 b values, an $S_0$ value, and a number of randomization repetitions;
 b) Select a range for the fitted parameter and SNR values, and a step size for each;
 c) Selecting a unique pair of base values for the fitted parameter and SNR within the selected range;
 d) Calculating $S_1 \ldots S_n$ values using Eq. [1], the selected b values, and a particular fitting technique;
 e) Calculating a standard deviation for signal noise based on the SNR value and an $S_i$ value;
 f) For each randomization repetition, generating a random Gaussian noise value based on the standard deviation for signal noise, adding the noise to the real and imaginary signal components, and calculating the magnitude of the complex noise for each b value;
 g) Calculate an ADC value based on the noise-based signal magnitudes using the fitting technique, and determine an error between base and fitted ADC values;
 h) Calculating a mean error for the current fitted parameter and SNR values;

i) Incrementing the fitted parameter and SNR values and repeating steps (c)-(h) until all pairs of values in the selected ranges have been calculated; and j) optionally generating an error map as a function of the fitted parameter and SNR values.

In certain embodiments, the fitted parameter can be the apparent diffusion coefficient (ADC). In further embodiments, the fitted parameter can be a T2 value, a T2* value, an R2 value, or an R2* value. In still further embodiments, the fitted parameters can be water and fat signal values ($M_w$ and $M_f$, respectively) and R2* values, and the $M_w$ and $M_f$ values fitted based on noise bias effects can be used to calculate proton density fat and water fractions.

In certain embodiments, the noise term can be a non-Gaussian noise term. In other embodiments the SNR range can be from less than 1 to about 20, or to about 50.

In further embodiments, an error map can be generated as a function of the base SNR and fitted parameter values. The axes of the error map can be presented in linear, nonlinear, and/or inverted forms.

In some embodiments, the error map can be used with error limit criteria to assess whether a particular combination of imaging protocol and fitting technique provides sufficiently low error estimates for the fitted parameter when noise bias effects are taken into account. Such error limit criteria can be used to modify imaging protocol parameters, either manually or automatically, to meet the criteria. In further embodiments, the error map can be used to correct the fitted parameter values to provide more accurate parameter values that account for noise bias effects directly.

In another embodiment, a system can be provided that includes an MRI system, a processor, and memory, such that the described methods can be applied to quantitative MRI data obtained by the MRI system using the processor and memory such that the noise-based errors in the fitted quantitative parameter can be assessed and maintained below a selected value by modifying one or more of the imaging protocol parameters. In a further embodiment, the calculated noise-based errors can be used as a correction factor to modify the fitted parameters obtained from the image data to yield improved estimates of the measured parameters.

BRIEF DESCRIPTION OF THE DRAWINGS

Further objects, features and advantages of the present disclosure will become apparent from the following detailed description taken in conjunction with the accompanying figures showing illustrative embodiments, results and/or features of the exemplary embodiments of the present disclosure, in which.

Throughout the drawings, the same reference numerals and characters, unless otherwise stated, are used to denote like features, elements, components, or portions of the illustrated embodiments. Similar features may thus be described by the same reference numerals, which indicate to the skilled reader that exchanges of features between different embodiments can be done unless otherwise explicitly stated. Moreover, while the present disclosure will now be described in detail with reference to the figures, it is done so in connection with the illustrative embodiments and is not limited by the particular embodiments illustrated in the figures. It is intended that changes and modifications can be made to the described embodiments without departing from the true scope and spirit of the present disclosure as defined by the appended claims.

DETAILED DESCRIPTION OF EXEMPLARY EMBODIMENTS

The present disclosure relates to a novel approach for estimating errors in fitted parameters for quantitative MRI procedures, and for obtaining improved parameter maps using quantitative MR imaging. Embodiments of the disclosure provide a method for predicting and estimating errors resulting from noise effects in the image data with low SNR that arise from any known or conventional fitting/calculation procedure to calculate the quantitative mapped parameters. Such error prediction can then be used to facilitate selection and optimization of MR imaging protocol parameters to reduce the errors in the determination of parameter maps as compared to other sub-optimal selections of imaging protocol parameters. This approach can also be used to compare the accuracy of different fitting/calculation methods to calculate the quantitative parameters using image data having different SNR values and/or noise characteristics. The error predictions can also be used to correct local fitted/calculated parameters directly to provide more accurate parameter maps that account for the noise-based errors inherent to the fitting procedure used. The disclosed methods can be used, e.g., with diffusion MR imaging to calculate an ADC map, and can also be applied to other quantitative MR imaging/mapping techniques for parameter estimation (linear or non-linear) where some source data are contaminated by noise of non-zero expectation value.

Figure 2:
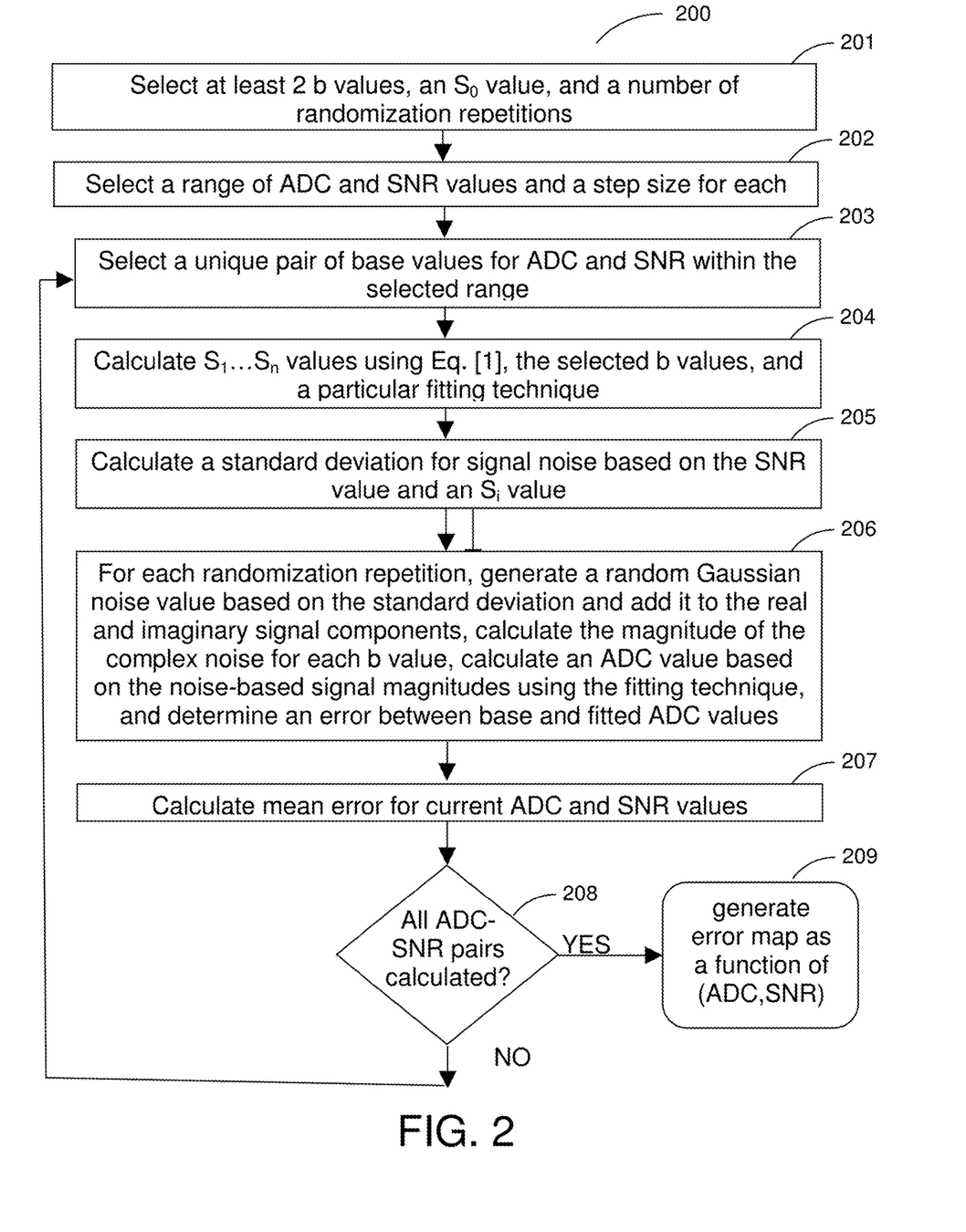
FIG. 2 is a flowchart illustrating the disclosed method for calculating errors in fitted quantitative MRI parameters based on noise bias effects.

Certain aspects of the disclosed method described below are shown in the flowchart of FIG. 2. This particular embodiment focuses on calculation of ADC maps, although it is noted that the same method can be used to determine other parameter maps using quantitative MRI procedures, as described elsewhere herein. Embodiments of the disclosure can provide calculated/estimated errors for calculated quantitative parameter values (and maps of such values) from MRI image data, where such errors may arise from both noise in the raw image data (e.g., diffusion-weighted MR data) and fitting techniques used to determine such parameter values from the raw image data. The resulting error values, which are a function of the parameter to be measured and an SNR of the imaging procedure, can then be used to select optimal imaging protocol that are sufficient to obtain accurate fitted parameter values while avoiding undesirable trade-offs such as excessively low image resolutions. Alternatively, the calculated error values/maps may be used to correct the fitted parameter values directly, thereby providing more accurate calculated parameter maps for a particular quantitative imaging procedure and set of imaging parameters.

An exemplary procedure 200 for determining noise-based errors in fitted ADC maps for a particular imaging protocol is illustrated in FIG. 2. First, a set of values of b is selected for the error map (step 201), corresponding to the b values that will be used in obtaining the DW image data using, e.g., an MRI system 1 as shown in FIG. 1. At least 2 b values are needed to solve for the ADC values, as noted herein above with respect to the description of Equation [1], because there are 2 variables to be determined in these equations (e.g., ADC and $S_0$), so at least 2 independent equations are needed to solve for these parameters. Typical values for b used in DW MRI are 50, 400, and 800 s/mm$^2$, although other values may be used as well. A base value for the parameter $S_0$ (representing the voxel signal intensity for imaging without diffusion weighting, e.g., for b=0) in Equation [1] is also selected (step 201). The value of this parameter can be on the order of about 1000. However, choice of the $S_0$ parameter is somewhat arbitrary, as it represents a constant scale factor that cancels out when fitting the calculated parameters and determining relative errors in such fitted calculations. Accordingly, $S_0$ may be selected to be unity to simplify calculations if desired.

In embodiments of the disclosure, a range of expected values of the parameter to be determined (e.g., an ADC) is selected, as well as a range of SNR values typical of the particular imaging protocol to be used (step 202). Incremental step sizes for each of these parameters (ADC, SNR) are also selected (step 202). For example, the SNR can typically range from about 0.1 to 50, and can be iterated with a step size of about 0.1. Similarly, the ADC can typically range from about 0.1×10$^{-3}$ mm$^2$/s to 5.0×10$^{-3}$ mm$^2$/s, and can be iterated with a step size of about 0.1×10$^{-3}$ mm$^2$/s. Such exemplary parameter ranges should cover most practical values that could occur with the clinical protocol. The iteration size can be small, such as with these exemplary values, to provide a detailed error map. Because the predicted errors are calculated numerically, using such increment sizes still allows computation of error maps for a particular protocol in reasonable times. In further embodiments, different ranges of SNR and ADC may be used based on the particular imaging procedure used and tissue(s) being imaged. The step size for each parameter may also be varied, depending on the desired degree of resolution of the error map and computational resources and times required.

Initial base values for ADC and SNR within their desired ranges are first selected (step 203). Then, an error calculation is performed for this pair of base parameter values (ADC, SNR), where the error is based on fitted/calculated values of ADC based on appropriate random noise values added to the corresponding base signal values $S_i$, as described in detail below.

For example, to calculate/predict noise-based errors for fitted quantitative MRI parameters, base values are first set for $S_0$, b, and the ADC as described above. $S_0$ is an arbitrary constant number, which may be set to unity if desired. The number and values of the b parameter can be selected to be the same as the b values that are used in the actual imaging protocol. A value for $S_i$ corresponding to each $b_i$ value is then calculated using the current value of ADC and the particular fitting method as applied to the signal equations, Eq. [1] (step 204).

A standard deviation for signal noise is then calculated using at least one $S_i$ value (from $S_0 \ldots S_n$) and the currently SNR value (step 205). A randomization procedure is then used with a selected number of repetitions to add random Gaussian noise to the real and imaginary parts of the complex signal data (step 206), where the complex signal data are generated using the signal model equations for the set of assumed b values (step 201) and the current base ADC value (step 203), and where the Gaussian noise has the standard deviation that was calculated based on $S_i$ and SNR (step 206). The number of Monte Carlo (or other randomization) repetitions can be any relatively large arbitrary number. For example, about 100 repetitions or more can be used, where a larger number of the randomization (e.g., Monte Carlo) repetitions can provide more accurate error estimations. The number of such repetitions can be limited by the computational resources required for the entire error-calculating procedure.

The magnitude of the resulting "noisy" complex signal data is then calculated for each b value for the desired number of repetitions, and used as the input data for the particular ADC fitting method selected to calculate a noise-based ADC value for the repetition (step 206). In one embodiment, the signal magnitudes can be averaged over all of the random noise repetitions for each b value, to obtain a single averaged noise effect for each b value (e.g., an "averaged b" approach). This averaged magnitude can then be used in the fitting procedure, where the number of equations being fitted (e.g., Eq. [1] or Eq. [3]) will equal the number of b values used. In another embodiment, each noise-based magnitude obtained from each randomization repetition for each b value can be used separately in the fitting procedure (e.g., a "non-averaged b" approach). In this embodiment, the number of equations being fitted (e.g., Eq. [1] or Eq. [3]) will equal the number of b values used multiplied by the number of randomization repetitions used for each b value.

An error is then calculated between the current base value of the ADC and the fitted ADC value that results from the simulated noise-based signal data and the selected fitting method for each repetition (step 206), and this error value can optionally be stored in memory. Mean and optionally standard deviation of these errors can then be calculated for each pair of SNR and ADC values after all randomization/Monte Carlo repetitions are completed (step 207). Thus, a comparison of the apparent ADC value (obtained by fitting the simulated noisy data) to the underlying assumed/base ADC value yields an error value for the fitted calculation of ADC at a given SNR value for the imaging protocol.

Then, the base ADC value and/or base SNR value can be incremented (steps 208 and 203) and the error calculation process can be repeated (steps 203-207), until the noise-based error for all ADC and SNR pairs over their respective ranges (based on the selected step size for each parameter) have been determined (step 207). The selection of unique base ADC and SNR values (steps 208, 203) can be done in any order, until error results for all pairs of SNR and ADC values in the range (using the selected increment for each parameter) have been calculated.

Lastly, an error map can be generated as a function of SNR and ADC (step 209). This error map represents the error between the assumed underlying ADC value and the ADC value that would be fitted based on noisy data at a particular SNR value. Such error information cannot be determined or reliably estimated from imaging data alone, as the true ADC values are not known a priori and can only be estimated by fitting the noisy image data. Accordingly, embodiments of the present disclosure provide a novel and nonobvious technique for accurately estimating errors in determining ADC values (or other quantitative MRI parameters) that result from fitting of inherently noisy image data.

In certain embodiments of the disclosure, the resulting error maps can be used to optimize imaging protocols to obtain accurate values for quantitative MRI parameters without unnecessarily sacrificing other information such as, e.g., image resolution. For example, based on the error map determined for a particular imaging protocol (which can affect SNR values), parameters of the protocol can be adjusted and the error map calculation can be repeated to lower the calculated errors in ADC (or other quantitative parameter) to an acceptable level. Such protocol parameters can include, but are not limited to, image resolution, number of signal acquisitions, etc., each of which can affect the SNR of the protocol in a manner known in the art.

In further embodiments, the error maps determined according to the methods described herein may be used to directly provide more accurate estimates of fitted quantitative parameters. For example, for a given imaging protocol, the ADC (or other parameter) values obtained by a selected fitting algorithm can be corrected by applying the calculated parameter errors from the map on a pixel-by-pixel or voxel-by-voxel basis. An error value can be determined for each pixel or voxel based on the fitted ADC value and the local SNR. This local error value can be used to correct the local fitted ADC value and provide a more accurate map of the ADC values that account for inherent noise in the MRI signals and the particular fitting method used for such signal data.

The method for calculating noised-based error maps for fitted quantitative MRI parameters described above and illustrated in FIG. 2 represent only one specific embodiment of the present disclosure. Various alternative or extended methods or details can be performed in further embodiments of the disclosure.

For example, in further embodiments, the SNR may be estimated from the non-diffusion weighted data or from a diffusion-weighted data with a low b value such as, e.g., b=50. In still further embodiments, a surrogate parameter for SNR may be used, such as the difference between the calculated values arising from two different ADC fitting methods for a particular set of signal data.

In other embodiments, the calculated error maps may be presented and/or adapted in a number of ways, depending on the particular needs for optimization or improvement of a particular quantitative MRI procedure. For example, one or both of the parameter scales (e.g., ADC or SNR) may be inverted or presented in a non-linear fashion. The error values may also represent the standard deviation or some other measure of the Monte Carlo/randomization simulation. Further, the calculated noise-based error may be expressed as a percentage of the parameter value, or as a simple numerical difference between noise-free and noise-based fitted parameter values.

The quantitative parameter error maps as described herein may be utilized in various ways, including both manual and automatic implementations. For example, in an exemplary manual implementation, a protocol can be manually selected and a quantitative image data set acquired. Values for the SNR and ADC values can be measured/fitted based on the image data and protocol used. The measured/fitted SNR and ADC values can then be looked up on the SNR and ADC axes of the error map, and the corresponding estimated error (which may be expressed as a percentage or a difference) can be located. Then, the protocol can be accepted if the corresponding errors are smaller than a threshold error or otherwise meet any selected acceptability criteria, or the protocol can otherwise be rejected and the procedure can be repeated with a modified protocol until an acceptable one is found. The acceptability criteria can include, e.g., limits on error values corresponding to particular regions of imaged tissue and/or particular value ranges for one or both parameters (ADC, SNR).

For an exemplary automatic implementation of the methods described herein, an initial quantitative image data set can be acquired and the SNR and ADC can be measured/fitted based on such data. The local SNR and ADC values can then be looked up on the SNR and ADC axes of the error map, such that the corresponding estimated noise-based errors can be determined. An automated procedure can be implemented to determine whether the protocol meets the acceptability criteria based on these error values, and a modification to the protocol may be generated automatically based on the determined error values. Further image data sets can be obtained, noise-based errors for the protocol determined, and further modifications to the protocol can be performed in a similar manner until a protocol is determined that meets the acceptability criteria.

Example: Calculation of T2, R2, T2* or R2* Maps

The systems and methods of the present disclosure can be extended to predict errors and optimize the protocols to calculate T2, R2, T2*, or R2* maps in spin echo (SE), turbo/fast spin echo (TSE/FSE), or gradient echo (GRE) MRI, respectively. Application of the disclosed systems and methods can be based on adaption of the applicable model equations appropriately, as described in more detail below.

For R2 calculations, the signal intensity typically is measured with a SE or TSE sequence. In contrast, for the R2* calculation, the signal intensity typically is measured with a GRE sequence. The equations and descriptions provided below are based on the example of calculating an R2 map, but they can be applied to both R2 and R2* map calculations, because their signal model equations have the same form.

For image data acquisitions used to calculate an R2 map, all imaging parameters except for the TE values (e.g., TR and flip angle) are kept constant so that common factors such as T1 effects can be ignored in the signal model. For n acquisitions with TE values that vary, the general equations of the acquired MR signal are given by $$S_1 = S_0 e^{-TE_1 \cdot R2}$$

$$\ldots,$$

$$S_n = S_0 e^{-TE_n \cdot R2} \qquad [11]$$

where $S_0$ is the pixel intensity corresponding to TE=0. The two unknown variables, $S_0$ and R2, can be determined using acquisitions with two or more different TE values.

Similarly, in order to apply an LL fitting procedure to determine S0 and R2 values, the log of both sides of Eq. [11] can be taken (using the definitions provided for Eqs. [2], [5], and [6] herein) to yield:

$$y_1 = \log(S_0) - R2 \cdot TE_1$$

$$y_n = \log(S_0) - R2 \cdot TE_n \qquad [12]$$

By defining:

$$x_i = TE_i, \qquad [13]$$

R2 can be calculated using the LL method as $$R2 = \frac{n\overline{xy} - \sum_{i=1}^{n} x_i y_i}{\sum_{i=1}^{n} x_i^2 - n\overline{x}^2}. \qquad [14]$$

To obtain the R2 noise-based error prediction results using the methods described herein, Eqs. [8]-[10] are still applicable except that Eq. [9] is replaced with:

$$m_0(TE_i) = S_0 e^{-TE_i \cdot R2}. \qquad [15]$$

After the R2 or R2* values are obtained using the desired fitting technique, the corresponding T2 and T2* values can be easily determined as:

$$T2 = 1/R2, \qquad [16]$$

and $$T2^* = 1/R2^*. \qquad [17]$$

Thus, errors arising from noise in MR signals can be calculated (and an error map produced) in a manner analogous to that described for calculating ADC maps herein above (and illustrated in FIG. 2) using Eqs. [8] and [10]-[17].

Example: Calculation of Proton Density Fat Fraction, Proton Density Water Fraction T2*/R2* or T2/R2 Maps The exemplary method and apparatus described herein can be extended to calculate proton density fat fraction (PDFF), proton density water fraction (PDWF), T2, R2, T2*, or R2* maps in SE, TSE/FSE or GRE MRI, respectively. For the R2 calculation, the signal intensity typically is measured with a SE or TSE sequence. In contrast, for the R2* calculation, the signal intensity typically is measured with a GRE sequence. Both sequences can generate the PDFF and PDWF maps. The equations and descriptions in this example are based on the example of calculating the R2* map described above, but they can be applied to both R2 and R2* because their signal model equations have the same form.

Embodiments of the present disclosure that extend applications of the noise-based parameter error calculations to proton density fat and water fractions can be based in part on the concepts described, e.g., in U.S. Patent Application No. US20140126795 of X. Zhong et al. The exemplary method described in this section is based on the assumption that water and fat have the same T2*/R2* value (a single effective T2*/R2* ratio), to more closely correspond to the examples described previously. However, the same concepts can also be extended to more general scenarios, e.g., where the T2*/R2* values of water and fat may be considered to be different, again based in part on the concepts described, e.g., in U.S. Patent Application No. US20140126795 of X. Zhong et al.

In one embodiment, sufficiently low flip angles are utilized in the data acquisition, so that $T_1$ effects can be neglected. All imaging parameters except the TE values, e.g. TR and flip angle, are kept the same. For the n acquisitions with TE values that are not completely the same, at the n-th echo time ($TE_n$), the general equation for the acquired MR signal can be represented by:

$$|S_n| = |(M_w + c_n M_f) \cdot e^{-R2^* TE_n}|. \qquad [18]$$

In this equation, there are three unknown values to fit: $M_w$ and $M_f$ are the water and fat signal magnitudes, respectively, which are proportional to the magnetization or proton density of those tissue types; and R2* is the transverse relaxation rate of the water and fat mixture (assuming water and fat have the same R2*).

The parameter $c_n$ in Eq. [18] represents the complex coefficient at $TE_n$ due to the difference of fat and water in the spectrum, and can be calculated based on the specific fat content in the body region of interest. In one embodiment, the complex coefficient $c_n$ can be calculated as $$c_n = \sum_{i=1}^{m} w_i e^{j(2\pi \Delta f_i TE_n)}, \qquad [19]$$

where m is the number of the fat spectral peaks in the model, and $w_i$ and $\Delta f_i$ are the fat peak weighting factors and the resonance frequency offsets relative to the water peak on the spectrum, respectively. In another embodiment, $c_n$ can be calculated based on the time-domain calibration of fat signal dephasing using the free induction decay signal from a multiple echo single-voxel spectroscopy measurement using the stimulated echo acquisition mode (STEAM) technique.

For the present example, Eqs. [8] and [9] can be modified as $$E = \sum_{i=1}^{n} \||S_i| - |F_i|\|^2, \qquad [20]$$

and $$m_0(TE_i) = (M_w + c_n M_f) \cdot e^{-R2^* TE_n}. \qquad [21]$$

Using these equations, a method similar to that described herein and shown in FIG. 2 for ADC error calculations can be applied to fit the $M_w$, $M_f$ and R2* parameters while accounting for noise bias in the fitted parameter calculations. The PDFF and PDWF values can be then calculated as $$PDFF = \frac{M_f}{M_w + M_f} \qquad [22]$$

and $$PDWF = \frac{M_w}{M_w + M_f}. \qquad [23]$$

Calculation of T1 Maps

Further embodiments of the disclosed method and apparatus can be used to calculate T1 maps in SE or TSE/FSE MRI. For example, to measure the longitudinal relaxation time T1 of each sample, an inversion recovery (IR) TSE sequence can be used to obtain images at different inversion times (TI). The signal equation for each $TI_n$ can be represented by:

$$S_n = K(1 - 2e^{-TI_n/T1} + e^{-TR/T1}),\qquad [24]$$

where K is the signal intensity in the absence of $T_1$ weighting. K and TI are the unknown values to be determined by a selected fitting procedure.

To obtain the T1 noise-based error results using the disclosed method, Eqs. [8]-[10] are still suitable except that Eq. [9] is replaced with:

$$m_0(TI_i) = K(1 - 2e^{-TI_i/T1} + e^{-TR/T1})\qquad [25]$$

Using these equations, a method similar to that described herein and shown in FIG. 2 for ADC error calculations can be applied to determine the K and T1 values using a fitting procedure, and to calculate errors in the fitted values arising from signal noise bias.

Sample Computational Results

Exemplary results of the quantitative MRI method for determining fitted parameter errors arising from signal noise bias using four different ADC fitting methods are shown FIGS. 3A-3C and FIGS. 4A-4D. In these figures, LL represents a log-linear fitting method, LS represents a least-squares fitting method, and LS MP-Cor represents the fitting method based on $m_{MP}$ and the Backward Approach (least-squares with MP correlation) as described in U.S. Patent Publication No. 2016/0084929 of Dale et al. Also, AveB indicates that an average was taken over multiple b values, whereas Non-AveB indicates that noise results were calculated for each b value separately. It is again noted that embodiments of the present disclosure can be used with any known fitting technique, and these four techniques are merely used as examples.

Figure 3A:
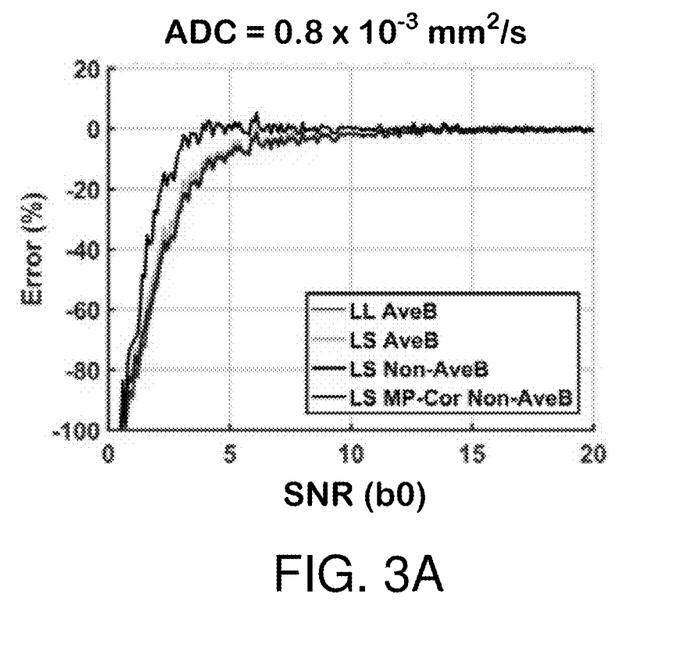
FIG. 3A is an exemplary graph of ADC parameter errors as a function of SNR for four fitting techniques with an ADC value of $0.8 \times 10^{-3}$ mm$^2$/s.
Figure 3B:
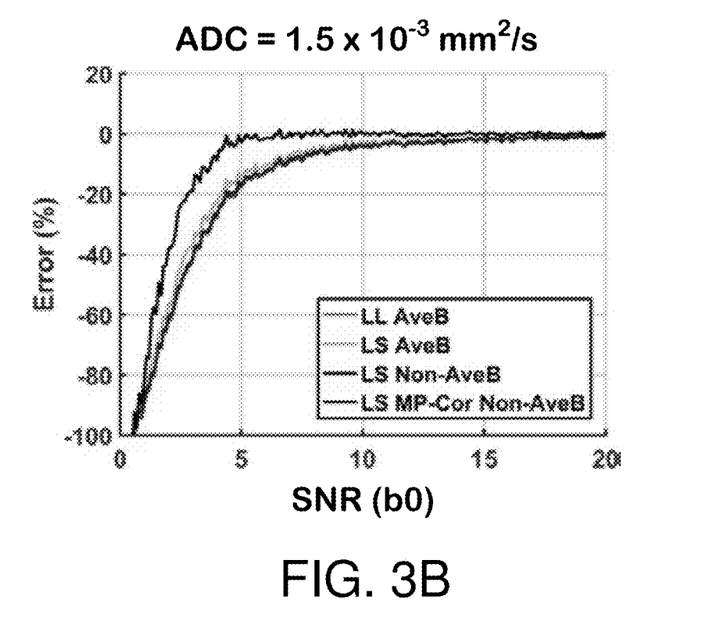
FIG. 3B is an exemplary graph of ADC parameter errors as a function of SNR for four fitting techniques with an ADC value of $1.5 \times 10^{-3}$ mm$^2$/s.
Figure 3C:
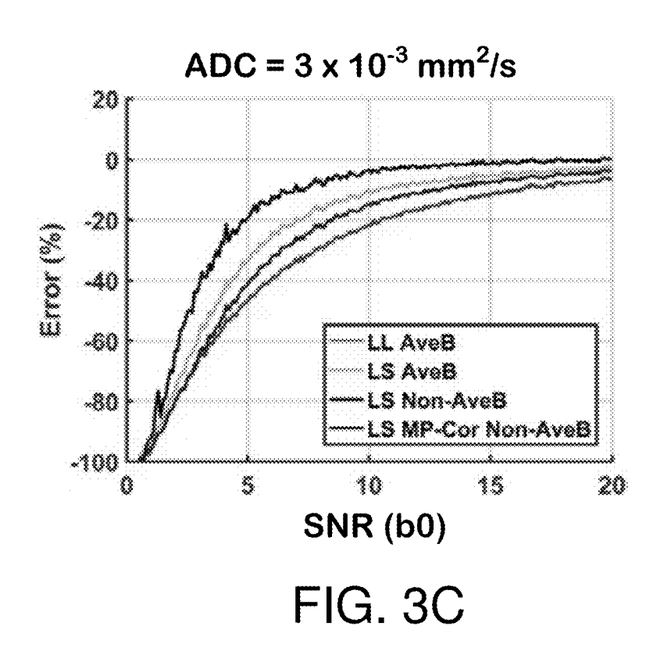
FIG. 3C is an exemplary graph of ADC parameter errors as a function of SNR for four fitting techniques with an ADC value of $3 \times 10^{-3}$ mm$^2$/s.
Figure 4A:
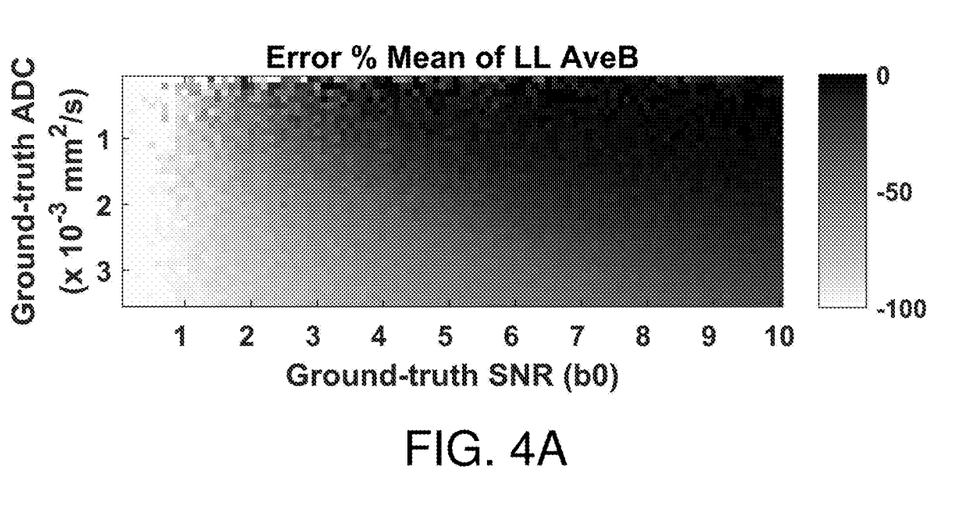
FIG. 4A is a calculated error map for ADC and SNR values based on noise bias effects using the LL AveB fitting technique.
Figure 4B:
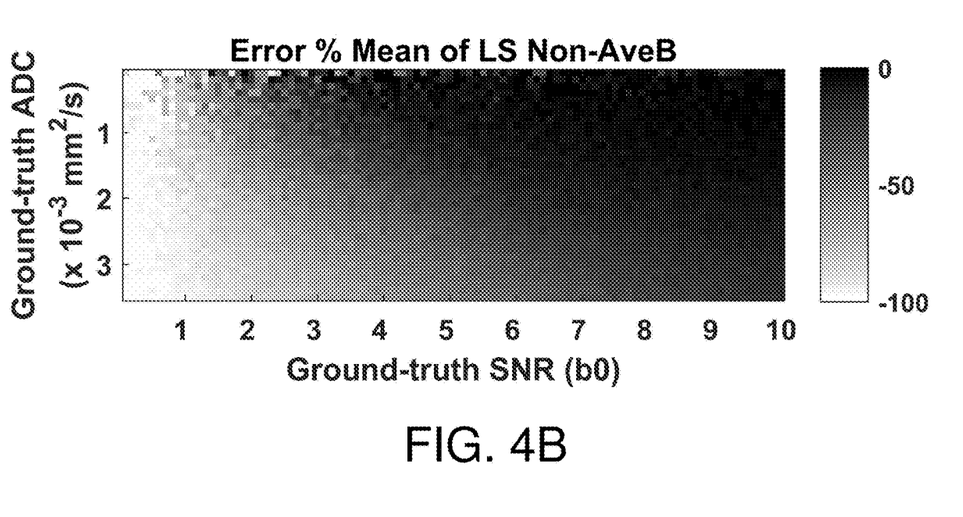
FIG. 4B is a calculated error map for ADC and SNR values based on noise bias effects using the LS Non-AveB fitting technique.
Figure 4C:
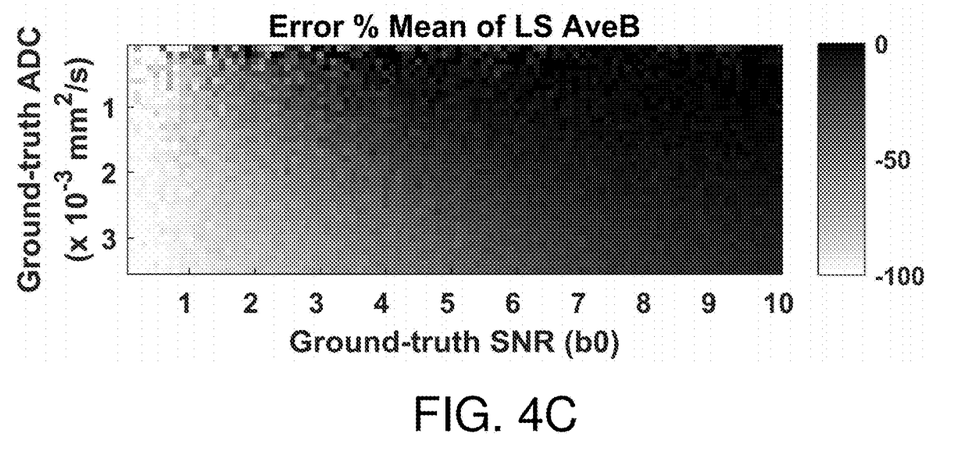
FIG. 4C is a calculated error map for ADC and SNR values based on noise bias effects using the LS AveB fitting technique.
Figure 4D:
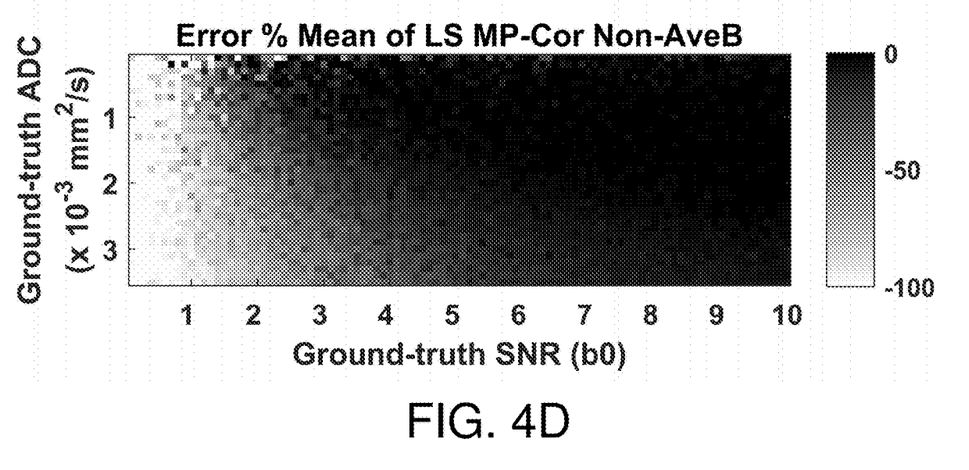
FIG. 4D is a calculated error map for ADC and SNR values based on noise bias effect using the LS MP-Corr Non-AveB fitting technique.

FIGS. 3A-3C show the calculated noise-based error % vs. SNR (b0) profiles for three typical ADC values using four different ADC fitting methods. These results were obtained using the exemplary error calculation approach described herein and illustrated in FIG. 2. The computations used to obtain these noise-based ADC error values were performed with b=50, 400, and 800 s/mm², with 2, 4, and 8 repetitions/averages, respectively. The SNR ranged from 0.1 to 20 with a step size of 0.1. The repetition number of Monte Carlo randomization steps for each SNR value was 500.

In FIG. 3A, with ADC=$0.8 \times 10^{-3}$ mm²/s, all four fitting techniques lead to large errors in calculated ADC values for small SNR values (e.g., less than about 2-3) when noise bias effects are ignored. The LS MP-Cor Non-AveB curve is the leftmost curve, which results in smaller errors than the other fitting techniques for SNR values of about 1-8. The other three fitting techniques yield very similar error values over the entire SNR range.

In FIG. 3B, with ADC=$1.5 \times 10^{-3}$ mm²/s, the LS MP-Cor Non-AveB (leftmost) curve results in significant errors in ADC values for SNR values up to about 4. The other three fitting techniques yield very similar error values over the entire SNR range, with significant errors (e.g., greater than about 5%) for SNR values up to about 10.

In FIG. 3C, with ADC=$3 \times 10^{-3}$ mm²/s, the LS MP-Cor Non-AveB (leftmost) curve again results in smaller errors than the other fitting techniques, with significant errors in ADC values (e.g., greater than about 5%) for SNR values up to about 10. The LS AveB technique is second leftmost, and yields lower errors than the other two techniques, with significant errors in ADC values (e.g., greater than about 5%) for SNR values up to about 15. The LS Non-AveB technique is third leftmost, and yields larger errors than the LS MP-Cor Non-AveB and LS AveB techniques for each SNR value, with significant errors in ADC values (e.g., greater than about 5%) for SNR values up to about 20. The LL AveB (rightmost) curve results in larger errors than the other fitting techniques for each SNR value, with an error in ADC values of about 8% for an SNR value of 20.

In each of these figures, it is seen that the error in fitted ADC values that do not consider noise bias decreases with increasing SNR, as expected. (Larger SNR values reduce the effects of noise relative to the signal.) Further, by comparing FIGS. 3A, 3B, and 3C, it is seen that noise bias has a greater effect with increasing ADC value, with larger errors in the fitted ADC value (that ignore noise bias) for each SNR value as the ADC value increases. It is also noted that according to FIGS. 3A-3C, the LS MP-Cor Non-AveB fitting technique provides the best accuracy with respect to ADC values when accounting for noise bias effects at a given SNR.

FIGS. 4A-4D show mean error % maps for ADC values as a function of SNR values for each of the four different fitting techniques. In each of these figures, the "Ground-truth" value represents the selected parameter value (step 203 in FIG. 2) used to simulate random noise effects and calculate noise-bias errors. The error maps in FIGS. 4A-4C were obtained using the following computational parameters: b=50, 400, and 800 s/mm², with 2, 4, and 8 repetitions/averages, respectively; the SNR ranged from 0.1 to 20 with a step size of 0.1; the ADC ranged from $0.1 \times 10^{-3}$ mm²/s to $3.5 \times 10^{-3}$ mm²/s, with a step size of $0.1 \times 10^{-3}$ mm²/s, and the repetition number of Monte Carlo randomization steps for each SNR/ADR pair was 120.

The darker area in each map indicates smaller fitting errors when ignoring noise bias effects, and the lighter (white) areas indicate larger errors, as shown on the scale to the right of each figure. Again, consistent with FIGS. 3A-3C, the error values are larger at small SNR values, and decrease with increasing SNR. The LL AveB error map in FIG. 4A indicates the largest errors at higher SNR values, followed by the LS Non-AveB fitting method in FIG. 4B, with somewhat smaller errors for corresponding ADC/SNR pairs. The LS AveB fitting technique in FIG. 4C leads to still smaller errors in ADC values for corresponding ADC/SNR pairs, and the LS MPCor Non-AveB fitting technique in FIG. 4D yields the smallest errors in ADC values for corresponding ADC/SNR pairs.

Each of the error maps in FIGS. 4A-4D indicate that errors in fitted ADC values when ignoring noise bias effects increase with smaller SNR values and larger ADC values, regardless of the fitting method used. As noted above, such error maps can be used to either assess acceptable parameter error limits for a particular imaging protocol, or alternatively, to provide an approximate correction factor for fitted parameters that accounts for noise bias effects and the particular fitting technique used.

The foregoing merely illustrates the principles of the present disclosure. Various modifications and alterations to the described embodiments will be apparent to those skilled in the art in view of the teachings herein. It will thus be appreciated that those skilled in the art will be able to devise numerous techniques which, although not explicitly described herein, embody the principles of the present disclosure and are thus within the spirit and scope of the present disclosure. Further, it is noted that all patents and publications identified in the present disclosure are incorporated herein by reference in their entireties.

What is claimed is:

1. A method for assessing errors in a fitted parameter in a quantitative MRI procedure using a particular imaging protocol, where such errors arise from signal noise effects and the fitting technique used, where the method comprises:

a) Selecting a plurality of b values, an $S_0$ value, and a range for both the fitted parameter and SNR values; and b) for each of a plurality of distinct pairs of base SNR values and base fitted parameter values within the selected range:

i. calculating $S_1 \ldots S_n$ values based on the selected b values and a particular fitting technique;

ii. selecting a standard deviation for signal noise based on the base SNR value and an $S_i$ value;

iii. for each of a plurality of iterations and for each b value:

generating a random noise value based on the standard deviation for signal noise; adding the random noise value to real and imaginary signal components determined from the b value, $S_0$ value, and base fitted parameter value; calculating a magnitude of the resulting complex signal; calculating a noise-based fitted parameter based on the magnitude of the resulting complex signal; and determining an error between the base fitted parameter value and the noise-based fitted parameter.

2. The method of claim 1, further comprising:

c) generating an error map based on the error determined between the base fitted parameter value and the noise-based fitted parameter as a function of each pair of base SNR values and base fitted parameter values.

3. The method of claim 1, wherein the random noise value is further based on a Gaussian distribution of noise values.

4. The method of claim 1, wherein the fitted parameter is an apparent diffusion coefficient (ADC).

5. The method of claim 1, wherein the fitted parameter is at least one of R2, R2*, T2, and T2*.

6. The method of claim 1, further comprising:

selecting a predetermined error limit;

determining whether any error between the base fitted parameter value and the noise-based fitted parameter for any pair of base fitted parameter value and base SNR value is greater than the predetermined error limit; and at least one of rejecting results of the quantitative MRI procedure, or modifying at least one parameter of the particular imaging protocol.

7. The method of claim 1, further comprising:

using the errors between the base fitted parameter values and the noise-based fitted parameters to correct fitted parameters obtained from the quantitative MRI procedure and the particular fitting technique.

8. The method of claim 1, wherein the particular fitting technique is at least one of a least-squares non-linear technique or a log-linear fitting technique.

9. The method of claim 1, further comprising performing steps a) and b) using a second fitting technique, and using the errors between the base fitted parameter value and the noise-based fitted parameter determined for each of the particular fitting technique and the second fitting technique to determine the relative accuracy of the particular fitting technique and the second fitting technique when signal noise effects are accounted for.

10. A system for improved quantitative MRI imaging, comprising:

an MRI system configured to obtain quantitative MRI image data and determine a local fitted parameter based on the image data and a fitting technique; and a processing unit configured to perform the following steps:

based on a predetermined plurality of b values, an $S_0$ value, and a range for both the fitted parameter and SNR values:

for each of a plurality of distinct pairs of base SNR values and base fitted parameter values within the predetermined ranges:

i. calculate $S_1 \ldots S_n$ values based on the selected b values and a particular fitting technique;

ii. select a standard deviation for signal noise based on the base SNR value and an $S_i$ value;

iii. for each of a plurality of iterations and for each b value:

generate a random noise value based on the standard deviation for signal noise; add the random noise value to real and imaginary signal components determined from the b value, $S_0$ value, and base fitted parameter value; calculate a magnitude of the resulting complex signal; calculate a noise-based fitted parameter based on the magnitude of the resulting complex signal; and determine an error between the base fitted parameter value and the noise-based fitted parameter.

11. The system of claim 10, wherein the processing unit is further configured to:

a) generate an error map based on the error determined between the base fitted parameter value and the noise-based fitted parameter as a function of each pair of base SNR values and base fitted parameter values.

12. The system of claim 10, wherein the random noise value is further based on a Gaussian distribution of noise values.

13. The system of claim 10, wherein the fitted parameter is an apparent diffusion coefficient (ADC).

14. The system of claim 10, wherein the fitted parameter is at least one of R2, R2*, T2, and T2*.

15. The system of claim 10, wherein the processing unit is further configured to:

determine whether any error between the base fitted parameter value and the noise-based fitted parameter for any pair of base fitted parameter value and base SNR value is greater than a predetermined error limit; and at least one of reject results of the quantitative MRI procedure, or modify at least one parameter of the particular imaging protocol.

16. The system of claim 10, wherein the processing unit is further configured to:

use the errors between the base fitted parameter values and the noise-based fitted parameters to correct fitted parameters obtained from the quantitative MRI procedure and the particular fitting technique.

17. The system of claim 10, wherein the particular fitting technique is at least one of a least-squares non-linear technique or a log-linear fitting technique.

18. The system of claim 10, wherein the processing unit is further configured to perform all of the recited steps using a second fitting technique, and use the errors between the base fitted parameter value and the noise-based fitted parameter determined for each of the particular fitting technique and the second fitting technique to determine the relative accuracy of the particular fitting technique and the second fitting technique when signal noise effects are accounted for.

* * * * *